US005763447A

United States Patent [19]

Jacobus et al.

[11] Patent Number: 5,763,447

[45] Date of Patent: Jun. 9, 1998

[54] METHOD OF PREVENTING OR TREATING PNEUMONIA IN IMMOBILIZED PATIENTS WITH URIDINE TRIPHOSPHATES AND RELATED COMPOUNDS

[75] Inventors: Karla M. Jacobus, Cary, N.C.; H. Jeff Leighton, Brookline, Mass.

[73] Assignee: Inspire Pharmaceuticals, Durham, N.C.

[21] Appl. No.: 685,216

[22] Filed: Jul. 23, 1996

[51] Int. Cl.$^6$ .......................... A61K 31/52; A61K 31/505

[52] U.S. Cl. .......................... 514/265; 514/266; 514/269; 514/274; 514/382; 544/243; 544/256; 544/264; 544/267; 544/268; 544/277; 544/315

[58] Field of Search .................................... 514/265, 266, 514/274, 382; 544/243, 256, 264, 267, 268, 277, 315

[56] References Cited

U.S. PATENT DOCUMENTS

| | | | |
|---|---|---|---|
| 5,292,498 | 3/1994 | Boucher | 424/45 |
| 5,420,116 | 5/1995 | Puchelle et al. | 514/47 |

FOREIGN PATENT DOCUMENTS

| | | |
|---|---|---|
| 2677250 | 5/1991 | France . |
| 2684299 | 2/1992 | France . |
| WO9211016 | 9/1992 | WIPO . |

OTHER PUBLICATIONS p. 520 "Mecial–Surgical Nursing: Assessment and Management of Clinical Problems" by S. Lewis and I. Collier, 2nd ed. 1987, McGraw–Hill, New York.

I. Kappestein, et al. *Eur. J. Clin. Microbiol. Infect. Dis.* 11(6), 504–8 (1992).

B. deBoisblanc, et al., *Chest* 103, 1543–7 (1993).

D. Craven, et al. *Am. Rev. Respir. Dis.* 133, 792–6 (1986).

T. Inglis, *J. Hosp. Infect.* 30, 409–13 (1995).

P. Mahul, et al. *Intensive Care Med.* 18, 20–5 (1992).

F. Konrad, et al. *Intensive Care Med.* 21, 482–89 (1995).

N. Cusack & S. Hourani, *Annals N.Y. Acad. Sc.* 603, 172–81 (Entitled "Biological Actions of Extracellular ATP"), 1987.

Kenner, et al., *J. Chem. Soc.* 1954, 2288.

Hall and Khorana, *J. Am. Chem. Soc.* 76, 5056 (1954).

Merck Index, Monograph No. 9795 (11th Ed. 1989).

R. Goody & F. Eckstein, *J. Am. Chem. Soc.* 93, 6252 (1971).

E. Rapaport, et al, *Proc. Natl, Acad. Sci. USA* 78, 838–42 (1981).

K. Ng and L.E. Orgel, *Nucleic Acids Res.* 15 (8) 3572–80 (1987).

D. Hoard and D. Ott, *J. Am. Chem. Soc.* 87, 1785–1788 (1965).

M. Yoshikawa, et al., *Tetrahedron Lett.* 5065–68 (1967).

J. Moffatt and H. Khorana, *J. Am. Chem. Soc.* 83, 649–59 (1961).

B. Fischer, et al., *J. Med. Chem.* 36, 3937–46 (1993).

N. Kotchetkov, et al., *Tetrahedron Lett.* 1993 (1971).

J. Barrio, et al., *Biochem. Biophys. Res. Commun.* 46, 597 (1972).

J. Secrist, et al., *Biochemistry* 11, 3499 (1972).

J. Bierndt, et al., *Nucleic Acids Res.* 5, 789 (1978).

K. Kayasuga–Mikado, et al., *Chem. Pharm. Bul.* (Tokyo) 28, 932 (1980).

J. Ludwig and F. Eckstein, *J. Org. Chem.* 54, 631–35 (1989).

G. Blackburn, et al., *J. Chem. Soc. Perkin Trans.* I, 1119–25 (1984).

T. Myers, et al., *J. Am. Chem. Soc.* 85, 3292–95 (1963).

F. Eckstein and R. Goody, *Biochemistry* 15, 1685 (1976).

F. Konrad, et al. *Chest* 105(1), 237–41 (1994).

F. Konrad, et al. *Chest* 102(5), 1377–83 (1992).

S. Mason, et al., *Br. J. Pharmacol.* 103, 1649–56 (1991).

M. Knowles, et al., *N. Engl. J. Med.* 325, 533–8 (1991).

R. Benali, et al., *Am. J. Respir Cell Mol. Biol.* 10, 363–8 (1994).

C. Jiang, et al., *Science* 262, 424–7 (1993).

D. Drutz, et al., abstract entitled "Uridine 5' Triphosphate (UTP) Regulates Mucociliary Clearance Via Purinergic Receptor Activation", presented at Purines '96 conference held in Milan, Italy Jul. 6–9, 1996.

H. Brown, et al., *Mol. Pharmacol.* 40, 648–55 (1991).

M. Lethem, et al., *Am. J. Respir. Cell Mol. Biol.* 9, 315–22 (1993).

S. Mason et al., *Am. Rev. Respir. Dis.* 147, A27 (1993).

C. Vallejo, et al., *Biochem. Biophys. Acata.* 438, 304–09 (1976).

M. Yoshikawa, et al., *Bul. Chem. Soc. (Jpn)* 42, 3505–08 (1969).

*Primary Examiner*—Ba K. Trinh

*Attorney, Agent, or Firm*—Albert P. Halluin; Howrey & Simon

[57] ABSTRACT

A method of promoting drainage of mucous secretions in the congested airways of a bedridden/immobilized patient or an intubated/mechanically-ventilated patient is disclosed. The method comprises administering to the airways of the patient a uridine phosphate such as uridine 5'-triphosphate (UTP) or $P^1,P^4$-di(uridine-5')tetraphosphate, an analog of UTP, or any other analog, in an amount effective to promote drainage of fluid in the congested airways, including sinuses, by hydrating mucous secretions or by stimulating ciliary beat frequency in the airways. Pharmaceutical formulations and methods of making the same are also disclosed. Methods of administering the same would include any liquid suspension (including nasal drops or eye drops or spray), oral form (liquid or pill), aerosol inhalation, powder form, topical, injected, intra-operative instillation or suppository form.

19 Claims, No Drawings

METHOD OF PREVENTING OR TREATING PNEUMONIA IN IMMOBILIZED PATIENTS WITH URIDINE TRIPHOSPHATES AND RELATED COMPOUNDS

TECHNICAL FIELD

This invention relates to a method of removing or preventing the accumulation of retained mucous secretions from the lungs and bronchi of immobilized or bedridden patients, including those whose breathing is assisted by mechanical ventilation.

BACKGROUND OF THE INVENTION

Bedrest or immobility can result from a variety of health problems, both acute and chronic in nature. A primary concern in caring for persons who are immobilized or placed on bedrest is that of prevention of pneumonia and other respiratory problems. Once pneumonia develops in these patients, morbidity and mortality can be significant. Because of the immobility it may be difficult for patients to cough and mobilize secretions. Immobile patients include patients confined to either beds or wheelchairs. In addition to complications arising from the immobility, the underlying health problem may place patients at increased risk for infection. Factors or disease states which predispose for high risk for pneumonia development include: altered conciousness (from head injury, anesthesia, drug overdose or other serious illness), tracheal intubation (via endotracheal, nasotracheal, or tracheostomy tubes), mechanical ventilation, and other procedures or treatments including intra-aortic balloon pump, hemo- or ultrafiltration, chronic disease states such as cancer, progressive neuromuscular disorders (multiple sclerosis, amytropic lateral sclerosis, etc.), heart disease, diabetes mellitus, acute neurological disorders (stroke, seizures, Guillain-Barre' syndrome, spinal cord injury), and rehabilitation from injuries or surgeries (bedrest, traction, etc.). (p. 502 "Medical-Surgical Nursing: Assessment and Management of Clinical Problems" by S. Lewis and I. Collier, 2nd ed. 1987, McGraw-Hill, New York).

Mechanical ventilation is indicated for respiratory failure or compromise resulting from a variety of pulmonary disorders and complications. It has been estimated that over 100,000 patients require mechanical ventilation in the U.S. every year (I. Kappstein, et al., *Eur. J. Clin. Microbiol. Infect. Dis.* 11(6), 504–8 (1992)). Morbidity and mortality from the underlying disorders can be high, and the addition of mechanical ventilation further increases risk. Complications resulting from mechanical ventilation may include: ventilator-associated pneumonia (VAP), pneumothorax, pulmonary embolus, right mainstem bronchus intubation, accidental extubation, aspiration of gastric contents, sepsis, fluid overload/heart failure, hypotension, and death (B. deBoisblanc, et al., *Chest* 103, 1543–7 (1993)). One of the most common complications is VAP, with an incidence conservatively estimated at 25%, with greater than 12,000 deaths per year due to VAP (D. Craven, et al., *Am. Rev. Respir. Dis.* 133, 792–6 (1986). Increased vigilance by nursing or other health care professionals, invasive monitoring, use of vasoactive medications, and frequent overall assessments greatly increase the cost of care for mechanically ventilated patients. A conservative estimate for total cost of these mechanically ventilated patients approaches $1.5 billion per year in the U.S. alone (I. Kappstein, supra).

Patients who are intubated and on mechanical ventilation are at several-fold higher risk for developing pneumonia and other pulmonary complications than non-intubated patients, due to the impairment or absence of several aspects of the normal pulmonary defense mechanisms (T. Inglis, *J. Hosp. Infect.* 30, 409–13 (1995)). Normal defense mechanisms consist of: 1) filtration, warming, and humidification of air; 2) epiglottis closure over the trachea; 3) cough reflex; 4) mucociliary escalator system; 5) immunoglobulins A and G; and 6) activity of alveolar macrophages. Airways distal to the larynx are normally sterile, but with intubation, the cough reflex is impaired and closure of the epiglottis cannot occur, allowing contamination of the lower airways. Because clinical practice guidelines generally do not advocate the maintenance of a complete airway seal in the trachea by the endotracheal cuff, some leakage of nasopharyngeal secretions below the epiglottis may occur, therefore increasing risk for infection in the lower airways (P. Mahul, et al., *Intensive Care Med.* 18, 20–5 (1992)).

The leading cause of VAP is thought to be aspiration of colonized gastric secretions via the incompletely closed glottis (P. Mahul, et al., supra). Colonization of the lower respiratory tract, especially with gram-negative bacteria is an early stage in the development of VAP. In addition, the use of suction catheters via the endotracheal tube to clear lower airway secretions, as well as other manipulations of the ventilatory system, significantly increase the chance for nosocomial infection, especially pneumonia. The normal warming, humidification, and filtration mechanisms for distal airways are non-functional for intubated patients, and the underlying conditions of the patient, i.e., malnutrition, fluid and/or electrolyte imbalance, and infections, may further complicate a patient's prognosis.

Mucociliary transport velocity has been shown to be impaired in patients who are intubated and receiving mechanical ventilation (F. Konrad, et al., *Intensive Care Med.* 21, 482–89 (1995); F. Konrad, et al., *Chest* 105(1), 237–41 (1994); F. Konrad, et al., *Chest* 102(5), 1377–83 (1992)). Because movement and clearance of secretions is an important lung defense mechanism, any impairment of this function, in addition to the introduction of artificial airways, mechnical ventilation, and the underlying disease state, can severely compromise the pulmonary host defense mechanisms.

Agents that can obviate the need for intubation and mechanical ventilation, or reduce time on mechanical ventilation, thereby decreasing the incidence of complications such as VAP, would certainly have a significant impact in the critical care setting, both in terms of the health of the patient and the costs associated with treatment. Applicants have discovered that uridine 5'-triphosphate (UTP) and related nucleotide compounds modulate specific activities of human airway epithelial cells that are components of the mucociliary escalator. Transport of foreign particles out of the lungs via the mucociliary escalator relies on the integrated action of: 1) mucus secretion by goblet cells and submucosal glands which traps foreign particles; 2) cilia to propel the mucus out of the lungs; and 3) epithelial ion transport systems which maintain the ionic milieu of, and hence the viscosity of, airway surface liquid to allow effective ciliary beating. Application of extracellular UTP to the apical surface of normal human nasal epithelial cells in primary culture causes increased $Cl^-$ secretion in a concentration-dependent manner (S. Mason, et al., *Br. J. Pharmacol.* 103, 1649–56 (1991); M. Knowles, et al., *N. Engl. J. Med.* 325, 533–8 (1991)). This response was also observed in cultured nasal epithelial cells from cystic fibrosis (CF) patients (R. Benali, et al., *Am. J. Respir. Cell Mol. Biol.* 10, 363–8 (1994)). This increased $Cl^-$ transport has been associated with increased fluid transport across the epithelium (C. Jiang, et al., *Science* 262, 424–7 (1993)). In addition to these effects on $Cl^-$ and fluid transport, UTP has been shown to produce an increase in cilia beat frequency in cultured human epithelial cells from normal adult humans and CF patients (D. Drutz, et al., abstract entitled "Uridine 5' Triphosphate (UTP) Regulates Mucociliary Clearance Via Purinergic Receptor Activation", presented at "Purines '96" conference held in Milan, Italy, Jul. 6–9, 1996). These actions of UTP have been associated with an increase in intracellular calcium ion ($Ca^{++}$) due to stimulation of phospholipase C by the $P_{2Y2}$ receptor (H. Brown, et al., *Mol. Pharmacol.* 40, 648–55 (1991)). UTP has also been shown to increase the rate and total amount of mucin secretion by goblet cells in human airway epithelial explants (M. Lethem, et al., *Am. J. Respir. Cell Mol. Biol.* 9, 315–22 (1993)). These effects were observed in tissues from both healthy individuals and patients with CF.

As for secondary pharmacological effects, aerosol administration of UTP ($10^{-2}$M and $10^{-1}$M in nebulizer) to anesthetized and ventilated dogs had no significant effects on peak inspiratory airway pressure, mean pulmonary artery pressure, heart rate, cardiac output, thoracic aortic pressure, electrocardiogram, or arterial blood gases (S. Mason, et al., *Am. Rev. Respir. Dis.* 147, A27 (1993)). To test the effect of intravenous administration, sequential doses of intravenous UTP (0.1, 1, 3 and 5 mmoles/kg) were infused into anesthetized, ventilated dogs over 10 minutes produced no significant changes in mean pulmonary artery pressure, heart rate, cardiac output, or mean arterial pressure. Id.

Because UTP has been shown to acutely improve mucociliary clearance (MCC) by 2.5-fold in normal volunteers without significant effects (D. Drutz, supra), it is thought that MCC improvement in mechanically ventilated patients would prevent the pooling of secretions, the plugging of mucus, and the resulting infections and atelectasis. In addition, removal of pulmonary secretions by coughing or suctioning may be enhanced by hydrating and thinning mucus secretions. UTP may, therefore, provide a safe adjunct or alternative to $\beta_2$-adrenergic agonists for enhancing the removal of lung secretions in mechanically ventilated patients. Additionally, the improvement in MCC will enhance the patient's pulmonary host defense mechanisms, thus preventing ventilator-associated pneumonia (VAP) and other pulmonary complications, such as atelectasis. In addition, by acting on receptors in type II alveolar cells, UTP may enhance surfactant production and therefore help maintain optimal gas exchange and airway epithelium function in terminal small airways.

Applicant postulates that MCC in mechanically-ventilated patients can be improved by administering UTP and its related compounds as well as other nucleoside phosphates such as: $P^1,P^4$-di(uridine-5')tetraphosphate ($U_2P_4$); adenosine 5'-triphosphate (ATP); $1,N^6$-ethenoadenosine 5'-triphosphate; adenosine 1-oxide 5'-triphosphate; $3,N^4$-ethenocytidine 5'-triphosphate; or $P^1,P^4$-di(adenosine-5')tetraphosphate ($A_2P_4$) to the site of fluid congestion. UTP and $U_2P_4$ are the preferred embodiments of the present invention. By administering UTP or $U_2P_4$ prior to or soon after intubation, VAP and other associated complications of mechanical ventilation may be avoided. The method of the present invention may also be used to treat chronic bronchitis patients who develop respiratory distress that requires intubation. Finally, the method of the present invention may also be used to promote the drainage of retained mucous secretions in immobilized or bedridden patients.

SUMMARY OF THE INVENTION

A method of preventing or treating pneumonia, including ventilator-associated pneumonia (VAP) in a subject in need of such treatment is disclosed. The method of the present invention may also be used to promote the drainage of retained mucous secretions in immobilized or bedridden patients to prevent pneumonia. The method comprises administering to the patient a compound of Formula I, or a pharmaceutically acceptable salt thereof, in an amount effective to hydrate mucous secretions and stimulate ciliary beat frequency in the luminal epithelial cells of the airway passages:

Formula I

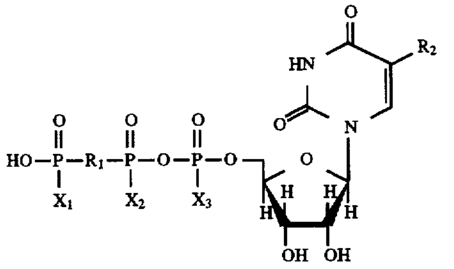

wherein:

$X_1$, $X_2$, and $X_3$ are each independently either $O^-$ or $S^-$. Preferably, $X_2$ and $X_3$ are $O^-$.

$R_1$ is O, imido, methylene, or dihalomethylene (e.g., dichloromethylene, diflouromethylene). Preferably, $R_1$ is oxygen or difluoromethylene.

$R_2$ is H or Br. Preferably, $R_2$ is H. Particularly preferred compounds of Formula I are uridine 5'-triphosphate [UTP] and uridine 5'-O-(3-thiotriphosphate) [UTPγS].

In addition to Formula I, Formula II, i.e., $P^1,P^4$-di(uridine-5')tetraphosphate [$U_2P_4$] is also a preferred embodiment of the invention. Another compound of Formula II is $P^1,P^4$-di (adenosine-5')tetraphosphate [$A_2P_4$]. The method of the present invention can also include administering a compound of Formula III (adenosine 5' triphosphate [ATP] or $1,N^6$-ethenoadenosine 5'-triphosphate or adenosine 1-oxide 5'-triphosphate), or Formula IV ($3,N^4$-ethenocytidine 5'-triphosphate).

Formula II

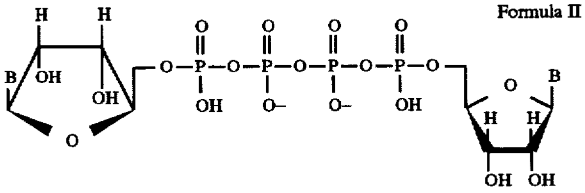

wherein:

B is uracil or adenine, attached as in Formulae I and III.

Formula III

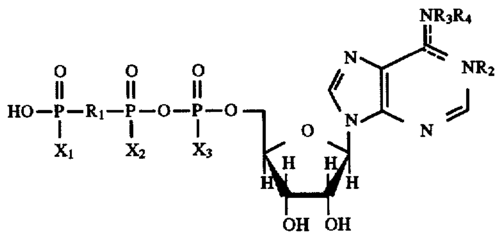

wherein:

$R_1$, $X_1$, $X_2$, and $X_3$ are defined as in Formula I.

$R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$ and $R_2$ taken together are —CH═CH—, forming a ring from N-6 to N-1 with a double bond between N-6 and C-6 (1,$N^6$-ethenoadenine).

Formula IV

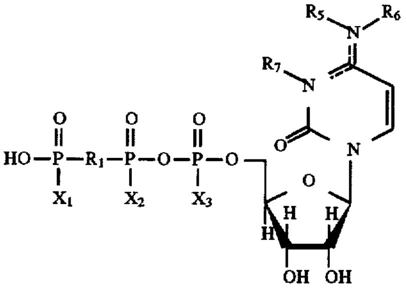

wherein:

$R_1$, $X_1$, $X_2$, and $X_3$ are defined as in Formula I.

$R_5$ and $R_6$ are H while $R_7$ is nothing and there is a double bond between N-3 and C-4 (cytosine), or, $R_5$, $R_6$ and $R_7$ taken together are —CH═CH—, forming a ring from N-3 to N-4 with a double bond between N-4 and C-4 (3,$N^4$-ethenocytosine).

A second aspect of the present invention is a pharmaceutical formulation containing the compound of Formula I, II, III or IV in an amount effective to hydrate mucous secretions and stimulate ciliary beat frequency in the luminal epithelial cells of the airway passages in a patient in need of such treatment.

A third aspect of the present invention is the use of the active compounds disclosed herein for the manufacture of a medicament for the therapeutic hydration of mucous secretions and stimulation of ciliary beat frequency in the luminal epithelial cells of the airway passages in a patient in need of such treatment.

The Description of the Specific Embodiments

The method of the present invention may be used to prevent or treat pneumonia, including ventilator-associated pneumonia (VAP) by hydrating retained mucous secretions and stimulating ciliary beat frequency in the airways of a subject in need of such treatment. The method of the present invention may also be used to prevent or treat sinusitis in nasally intubated patients, and to improve mucociliary clearance (MCC) thereby preventing pneumonia in chronically immobilized or bedridden patients. The present invention increases mucociliary clearance (MCC) in three ways: (1) by increasing the ciliary beat frequency of cilia on the surface of luminal epithelia cells, (2) by increasing the secretions of mucins by goblet cells, and (3) increasing the chloride ion secretion and simultaneously increasing the secretion of water into the periciliary liquid layer by luminal epithelial cells, consequently lowering the viscosity of the mucus. The mucins secreted by goblet cells form a layer on top of the cilia and capture foreign particles, including viruses and bacteria; the mucin layer is transported by the wave-like action of cilia; and the movement of cilia is facilitated by the hydration of the periciliary liquid layer surrounding the cilia.

Compounds illustrative of the compounds of Formula I above include: (a) uridine 5'-triphosphate (UTP); (b) uridine 5'-O-(3-thiotriphosphate) (UTPγS); and (c) 5-bromo-uridine 5'-triphosphate (5-BrUTP). These compounds are known or may be made in accordance with known procedures, or variations thereof which will be apparent to those skilled in the art. [See generally N. Cusack and S. Hourani, *Annals N.Y. Acad. Sci.* 603, 172–81 (entitled "Biological Actions of Extracellular ATP").] For example, UTP may be made in the manner described in Kenner, et al., *J. Chem. Soc.* 1954, 2288. Following this well-known methodology, UTP can be synthesized by condensing 2':3'-di-O-acetyl- or 2':3'-O-isopropylidine-uridine-5' benzyl phosphorochloridate with a salt of tribenzyl pyrophosphate and then removing the benzyl and other protecting groups. UTP has also been synthesized by treating at room temperature a mixture of UMP and 85% orthophosphoric acid with excess DCC in aqueous pyridine. Hall and Khorana, *J. Am. Chem. Soc.* 76, 5056 (1954).

The Merck Index, Monograph No.9795 (11 th Ed. 1989) gives the chemical structure of UTP;

S-2-carbamoylethyl thiophosphate can be used for the chemical synthesis of thiophosphate compounds such as UTPγS which has a sulfur at its terminal phosphorus atom. S. Goody and F. Eckstein, *J. Am. Chem. Soc.* 93, 6252 (1971).

For simplicity, Formulae I–IV herein illustrate the active compounds in the naturally occuring D-configuration, but the present invention also encompasses compounds in the L-configuration, and mixtures of compounds in the D- and L-configurations, unless otherwise specified. The naturally occuring D-configuration is preferred.

Compounds illustrative of the compounds of Formula II include (P1,P4-di(adenosine-5')tetraphosphate ($A_2P_4$) or P1,P4-di(uridine-5')tetraphosphate ($U_2P_4$). These compounds can be made in accordance with known procedures, or variations thereof. For example, $A_2P_4$ was synthetically prepared by activating ADP with carbonyldiimidazole. E. Rapaport, et al., *Proc. Natl. Acad. Sci. USA* 72(2), 838–42 (1981). Treating aqueous solutions of adenosine-5'-mono-, di-, or triphosphate with carbodiimide results in diadenosine-5'-5'-polyphosphate (including $A_2P_1$). K. Ng and L. E. Orgel, Nucleic Acids Res. 15 (8), 3572–80 (1987). $U_2P_4$ can be synthesized through the reaction of uridine 5'-phosphoromorpholidate (0.54 mmol) with triethylamine salt of pyrophosphate (0.35 mmol) in a medium of anhydrous pyridine (10 ml). C. Vallejo, et al., Biochem. Biophys. Acta 438, 304–09 (1976).

Compounds illustrative of the compounds of Formula III above include (a) adenosine 5'-triphosphate (ATP) and (b) 1,N6-ethenoadenosine 5'-triphosphate. Compounds illustrative of the compounds of Formula IV above include (a) cytidine 5'-triphosphate and (b) 3,N4-ethenocytidine 5'-triphosphate. These compounds can be made in accordance with known procedures, or variations thereof which will be apparent to those skilled in the art. For example, nucleoside triphosphates can be synthesized by the reaction of the phosphorimidazolidate formed from a nucleotide and 1,1'-carbonyldiimidazole with inorganic pyrophosphate. D. Hoard and D. Ott, *J. Am. Chem. Soc.* 87, 1785–1788 (1965). Another general method involves adding a 2',3'-isopropylidene nucleoside to a cold mixture of trialkyl, phosphate and phosphoryl chloride with stirring. The mixture is converted into the corresponding 5'-phosphorodichloridate. 5'nucleotide is obtained by rapid hydrolysis of the chloridate group followed by removal of the isopropylidene group at 70° C. M. Yoshikawa, et al., *Tetrahedron Lett.* 5065–68 (1967) and idem., *Bull. Chem. Soc. (Jpn)* 42, 3505–08 (1969).

Nucleoside-5' phosphoramidates may be used as an improved method for the preparation of nucleoside-5' polyphosphates. J. Moffatt and H. Khorana, *J. Am. Chem. Soc.* 83, 649–59 (1961); and B. Fischer, et al., J. Med. Chem. 36, 3937–46 (1993).

Etheno derivatives of cytidine and adenosine are prepared by known methods. For example, a reaction using chloroacetaldehyde and the nucleosides adenosine and cytidine is well known. Chloroacetaldehyde reacts with 9-N-inethyladenine and I-N-methylcytosine in weakly acidic aqueous solutions to form ethenoderivatives of cytidine and adenosine. N. Kotchetkov, et al., *Tetrahedron Lett.* 1993 (1971); J. Barrio, et al., *Biochem. Biophys. Res. Commun.* 46, 597 (1972); J. Secrist, et al., *Biochemistry* 11, 3499 (1972); J. Bierndt, et al., *Nucleic Acids Res.* 5, 789 (1978): K. Kovasuga-Mikado, et al., *Chem. Pharm. Bull. (Tokyo)* 28, 932 (1980).

Derivatives with alpha, beta and gamma thiophosphorus groups can be derived by the following or by adapting the following methods: 2-Chloro-4H-1,3,2-benzodioxaphosphorin-4-one can be used to phosphitylate the 5'-hydroxy group of a nucleoside to form an intermediate, which on a subsequent reaction with pyrophosphate forms, in a double displacement process a $P^2,P^3$-dioxo-P'-5'-nucleosidylcyclo triphophite. Oxidation with sulfur forms a nucleoside 5'-(1-thiocyclotriphosphate), which is hydrolyzed to the diastereomeric mixture of a nucleoside 5'-O-(1-thiotriphosphate). Alternatively, $P^2,P^3$-dioxo-P'-5'-nucleosidylcyclo triphophite can be oxidized with iodine/water to yield nucleoside 5'-triphosphates. This reagent can also be used for the synthesis of nucleoside 2',3'-cyclic phosphorothioates. J. Ludwig and F. Eckstein, *J. Org. Chem.* 54, 631–35 (1989).

Derivatives with alpha, beta and gamma thiophosphorus groups can also be made by following the protocol recited in F. Eckstein and R. Goody, Biochemistry 15, 1685 (1976). [$^{35}$S]Adenosine 5'-(0-1-thiotriphosphate). [$^{35}$S]Adenosine 5'-phosphorothioate (7500 $A_{260}$ units, 0.5 mmol) was converted to the pyridinium salt by passage over Merck I ion exchanger (pyridinium form). The solution was evaporated to dryness, tri-n-octylamine (0.22 ml, 0.5 mmol) and methanol (ca. 10 ml) were added, and the mixture was stirred until a clear solution was obtained. After evaporation, the residue was evaporated (three times) with dry dimethylformamide using an oil pump. The residue was dissolved in anhydrous dioxane (2 ml) and diphenyl phosphorochloridate (0.15 md, 0.75 mmol) and tri-n-butylamine (0.25 ml, 1 mmol) were added. After stirring the mixture at room temperature for 3 h, the solvent was removed by evaporation, and anhydrous ether (10 ml) and petroleum ether (30 ml) were added to the residue, and the mixture was left at 0° C. for 30 min. The ether was decanted, the remaining material dissolved in anhydrous dioxane (1 ml), and the solution evaporated.

Tetrasodium pyrophosphate decahydrate (2.23 g, 0.5 mmol) was converted to the pyridinium salt by addition of tri-n-butylamine (2.43 ml, 10 mmol) and evaporation to dryness to the tri-n-butylammonium salt. After repeated evaporation with anhydrous pyridine (three times), the material was dissolved in anhydrous pyridine (3 ml) and added to the activated [$^{35}$S]adenosine 5'-phosphorothioate described above.

After stirring at room temperature for 2 h, ether (10 ml) was added to precipitate the product. The precipitate was dissolved in water and chromatographed on a DE-52 cellulose column (37×2.5 cm), with a linear gradient of 1.5 l. Each of 0.05M and 0.5M triethylammoniium bicarbonate. The product was eluted at ca. 0.33M buffer, yield 1550 $A_{260}$ units (0.1 mmol, 20%). For further purification this material was rechromatographed on a OAE-A 25 Sephadex column (1.5×25 cm) with a linear gradient of 800 ml each of 0.25M and 0.5M triethylammonium bicarbonate: yield 1200 $A_{260}$ units (16%). The material was not degraded by snake venom phosphodiesterase but was degraded to AMPS[1] by alkaline phosphatase under conditions described for ATPβS;

[$^{35}$S]Adenosine 5'-(O-1-Thiodiphosphate). The synthesis of this compound was carried out as described for [$^{35}$S] adenosine 5'-(O-1-thiotriphosphate) except that phosphate was added to the activated [$^{35}$S]adenosine 5'-phosphorothioate instead of pyrophosphate: yield 1410 $A_{260}$ units (0.94 mmol, 18%).

Adenosine 5'-(O-2-thiotriphosphate) (ATPβS) Adenosine 5'-(O-2-thiodiphosphate (1.5 mmol; Goody and Eckstein, 1971) was converted to its pyridinium salt by passage over Merck I ion exchanger (pyridinium form) in methanol-water (1:1, v/v), and the solution was evaporated to dryness using a rotary evaporator. Tri-n-octylamine (1.3 ml, ca. 3 mmol) and methanol (10 ml) were added to the residue, and the mixture was stirred until solution was obtained (ca. 30 min). After removal of solvent under reduced pressure, the residue was dissolved in dry pyridine (10 ml) and evaporated to dryness on a rotary evaporator using an oil pump. This process was repeated three times.

β-Cyanoethyl phosphate ($Ba^{2+}$ salt, 854 mg, 3 mmol) was converted to its mon(tri-n-octylammonium) salt in a similar way to that described above, using 3 mmol of tri-n-octylamine. The salt was dried by repeated addition and reevaporation of dry dimethylformamide (10 ml) and then dissolved in dry dioxane (15 ml). Diphenyl phosphorochloridate (0.9 ml, 4.5 mmol) and tri-n-butylamine (0.45 ml) were added, and the solution was allowed to stand at room temperature for 3 h. After removal of dioxane under reduced pressure, ether (30 ml) followed by petroleum ether (60 ml; 60°–80° C.) was added and, after shaking for a few minutes, the mixture was allowed to stand for 15 min in ice. The ether was then removed by decantation and the residue dissolved in dry dioxane (5 ml) which was then removed by evaporation under reduced pressure, and to the residue was added the ADPβS tri-n-octylammonium salt, prepared as described above dissolved in a mixture of dry hexamethyl phosphorotriamidate (4 ml) and dry pyridine (4 ml). The resulting solution was allowed to stand for 3 h at room temperature, and pyridine was then removed under reduced pressure. The remaining mixture was treated with 0.5N sodium hydroxide (100 ml) for 1 h at room temperature, after which time the solution was neutralized by addition of Merck I ion exchanger (pyridinium form). The neutralized solution was applied to a column of DE-52-cellulose (ca. 50×4 cm) which was eluted with a linear gradient of triethylammonium bicarbonate (0.1–0.35M, 2×2 l.). The product was eluted at about 0.25M: yield 2750 $A_{260}$ units (12%); for $^{31}$PNMR spectrum, see Table I. This was slightly contaminated with ADPβS. A further 800 $A_{260}$ units of product were obtained, more heavily contaminated with ADPβS. Pure ADPβS could be obtained by chromatography on DEAE-Sephadex A-25, using a gradient of triethylammonium bicarbonate (0.2–0.5M) at 4° C. The product behaved identically with regard to TLC on PEI-cellulose with ATPβS synthesized using pyruvaate kinase.

R. Goody and F. Eckstein, *J. Am. Chem. Soc.* 93, 6252 (1971) describe the synthesis of thiophosphate analogs of nucleoside di- and triphosphates having a sulfur at the terminal phosphorus atom by the use of S-2-carbamoylethyl thiophosphate.

Compounds of Formulas I, III, or IV where $R_1$ is $CCl_2$ and $CF_2$ can be prepared by methods similar to that described in G. Blackburn, et al., *J. Chem. Soc. Perkin Trans.* I, 1119–25 (1984).

Adenosine 5'-(β,γ-μ-Difluoromethylene)triphosphate, $AMPPCF_2P$ (1c).—(α) Morpholine-4-N,N'-dicyclohexylcarboxamidinium adenosine-5'-phosphoromorpholidate (390 mg, 0.5 mmol) was dissolved in anhydrous, amine-free pyridine (5 ml). The solution was evaporated to dryness and the procedure repeated twice more with exclusion of moisture. It was finally dissolved in pyridine (3 ml). Similarly the bis(tri-n-butylammonium) salt of difluoromethylenebisphosphonic acid (580 mg, 1.0 mmol) was evaporated repeatedly from its solution in pyridine (3×5 ml). Finally, the two pyridine solutions were combined and evaporated to dryness. The residue was kept in anhydrous pyridine (4 ml) for 24 h with magnetic stirring and exclusion of moisture. After this time the solution was evaporated to remove pyridine. The residue was dissolved in deionized water (5 ml), applied to a column of DEAE-Sephadex (3×30 cm), and the product eluted with a linear salt gradient (0–0.5M-LiCl). Fractions containing the analogue were combined and evaporated to dryness. The white solid residue was dissolved in a small volume of anhydrous methanol (5 ml) and the nucleotide precipitated out by the addition of a acetone (25 ml). The precipitated product was collected by centrifugation and the whole procedure repeated four times. The white pellet was finally redissolved in methanol (10 ml) and evaporated to dryness to yield the white, powdery product as the tetralithium salt (164 MG, 54%), m.p. 225°–235° C. (decomp.).

Adenosine 5'-(β,γ-μ-Dichloromethylene)triphosphate, $AMPPCCl_2P$(1e). Adenosine-5'-phosphoromorpholidate (390 mg, 0.5 mmol) was condensed with the bis(tri-n-butylammonium) salt of dichloro-methylenebisphosphonic acid (613 mg, 1 mmol). The product was chromatographed on DEAE Sephadex using a linear gradient (LiCl, 0–0.5M, pH 7.0.2 1). Fractions containing the product were combined and evaporated to dryness and the product isolated by repeated dissolution in methanol (5 ml) and precipitation with acetone (25 ml) to give a white powder (24 mg, 75.7%), m.p. 235°–245° C. (decomp).

Preparation ofguanosine 5'-(β,γ-μ-Difluoromethylenetriphosphate) $GMPPCF_2P$ (2b)—Morpholine-4-N,N'-dicyclohexyl-carboxamidinium guanosine-5'-phosphoromorpholidate (390 mg, 0.5 mmol) was dissolved in a mixture of anhydrous pyridine (5 ml) and freshly distilled 2-chlorophenox (4 ml). To this was added the bis(tri-n-butylammonium) difluoromethylenebisphosphonate (580 mg, 1 mmol). The solution was stirred for 4 days with exclusion of moisture and light. After this time water (50 ml) was added and the solution extracted with ether (3×50 ml). The aqueous phase was evaporated to dryness and the gummy residue redissolved in water (5 ml), applied to a column of DEAE Sephadex and eluted with a linear salt gradient (LiCl, 0–0.5M, pH 7.0). Fractions containing the analogue were combined and evaporated to dryness and the product repeatedly precipitated from methanol with acetone. Evaporation to dryness of the final product in methanol yielded the title compound as a white powder (136 mg, 42.8%), m.p. 245°–255° C. (decomp.).

Guanosine 5'(β,γ-μ-Dichloromethylene)triphosphate $GMPPCCl_2P$ (2d).—In a reaction exactly analogous to that for (2b), morpholine-4-N,N'-dicyclohexylcarboxamidinium guanosine-5'-phosphoromorpholidate (144 mg, 0.2 mmol) was combined with the bis(tri-n-butylammonium) salt of dichloro-methylenebisphosphonic acid[10] (360 mg, 0.6 mmol) to yield the product as a white powder, (81 mg, 62%), m.p. 240°–260° C. (decomp).

Compounds of Formula I, II, III where $R_1$ is CH2 can be prepared by methods similar to that described in T. Myers, et al., *J. Am. Chem. Soc.* 85, 3292–95 (1963). This methodology demonstrates that the syntehsis of 5'-adenylylmethylene or diphosphonate has been accomplished by the reaction of adenosine 5'-phosphoromidate with methylenediphosphonic acid and by the condensation of AMP with methylenediphosphonic acid in the presence of excess dicyclohexylcarbodiimide.

In addition, UTP, ATP, CTP, $A_2P_4$, 3,$N^4$-ethenocytidine triphosphate, 1,$N^6$-ethenoadenine 5'-triphosphate, adenosine 1-oxide 5'-triphosphate, ATPγS, ATPβS, ATPαS, $AMPPCH_2P$, AMPPNHP, $N^4$-ethenocytidine and 1,$N^6$-ethenoadenosine are commercially available, for example, from Sigma Chemical Company, PO Box 14508, St. Louis, Mo. 63178.

The active compounds of Formulae I–IV may be administered by themselves or in the form of their pharmaceutically acceptable salts, e.g., an alkali metal salt such as sodium or potassium, an alkaline earth salt, or an ammonium and tetraalkyl ammonium salts, $NX_4^+$ (wherein X is $C_{1-4}$). Pharmaceutically acceptable salts are salts that retain the desired biological activity of the parent compound and do not impart undesired toxicological effects.

The active compounds disclosed herein may be administered to the lungs, sinuses, ears or eyes by a variety of suitable means, but are preferably administered by administering a liquid/liquid suspension (either a nasal spray of respirable particles which is either inhaled by the subject or administered to the subject by means of nebulization through the mechanical ventilation system, or nasal drops of a liquid formulation, or eye drops of a liquid formulation) comprised of the active compound. Liquid pharmaceutical compositions of the active compound for producing a nasal spray or nasal powder, nasal or eye drops, or a liquid nebulized preparation may be prepared by combining the active compound with a suitable vehicle, such as sterile pyrogen free water or sterile saline by techniques known to those skilled in the art.

The dosage of active compound to hydrate mucous secretions and stimulate ciliary beat frequency in the airways will vary depending on the state of the subject, but generally an effective amount is the amount sufficient to achieve concentrations of active compound on the airway passages of the subject of from about $10^{-7}$ to about $10^{-1}$ moles/liter (e.g., for UTP, from about 0.0001 mg/mL to about 50 mg/mL), and more preferably from about $10^{-6}$ to about $10^{-1}$ moles/liter (e.g., for UTP, from about 0.0001 mg/mL to about 50 mg/mL).

Depending upon the solubility of the particular formulation of active compound administered, the daily dose to promote fluid drainage may be divided among one or several unit dose administrations. Preferably, the number of daily doses is no more than four times per day.

Another means of administering the active compound to the airways of the patient to promote fluid/secretion drainage may include any oral form of the active compound, administered to the patient either by means of a liquid suspension of the active compound which is poured into the mouth of the patient, or by means of a pill form swallowed by the patient, or administered through a feeding tube.

Another means of administering an effective amount of the active compound to the airways would involve administering a nebulized form of the active compound into their respiratory tract, such that the active compound enters either the nasopharnyx or a nasotracheal tube, endotracheal tube, or tracheostomy and subsequently reaches the airways or sinuses either directly or via systemic absorption and circulation. The active compound can be aerosolized in a variety of forms, such as, but not limited to, dry powder inhalants, metered dose inhalants, or liquid/liquid suspensions. In dry powder delivery, the UTP may be formulated alone or in combination with a diluent or carrier, such as sugars (i.e., lactose, sucrose, trehalose, mannitol) or other acceptable excipients for lung or airway delivery. The dry powder may be obtained by methods known in the art, such as spray-drying, milling, freeze-drying, etc.

Another means of administering the active compound to the airways would include any topical form of the active compound, administered as a cream or gel to the nose, eyes or outer ear which would subsequently permeate into the sinus passages of the patient, or administered via a dermal patch, such that a therapeutically effective amount reaches the airways via systemic absorption and circulation.

Another means of administering the active compound to the airways would involve an injected form of the active compound, injected from the chest area or chest tube directly into the lungs.

Another means of administering the active compound to the airways would involve a suppository form of the active compound, such that a therapeutically effective amount of the compound reaches the airways via systemic absorption and circulation.

Another means of administering the active compound would involve intra-operative instillation of a gel, cream, powder, foam, crystal or liquid suspension form of the active compound such that a therapeutically effective amount reaches the airways.

The preferred embodiments of the present invention—UTP and $U_2P_4$, as well as the other compounds for Formulae I–IV also have therapeutic benefit when used in combination with other agents used to treat VAP and retained mucous secretions in immobilized or bedridden patients, such as, but not limited to: antibiotics; antiviral agents; vasoactive agents (such as dopamine, epinephrine, or sodium nitro-prusside); anti-ulcer agents; antacids; analgesics; sedatives; paralytics; anti-platelet adhesion agents (e.g., aspirin, etc.); anti-clotting, blood-thinning agents (e.g., heparin, warfarin, etc.); antihistamine/beta agonist decongestant agents; humidification systems to loosen airway mucus; chest physical therapy and physical activity to do the same; and therapeutic beds which mechanically rotate the patient in order to loosen mucous secretions.

The present invention is further explained in the Example which follows. This example is intended as illustrative of the invention, and is not to be taken as limiting thereof.

EXPERIMENTAL

EXAMPLE 1

Treatment of Patients At Risk For Ventilator-Associated Pneumonia (VAP)

Uridine 5'-triphosphate (UTP) or $P^1,P^4$ di(uridine-5') tetraphosphate ($U_2P_4$) is administered to adult patients with acute neurological impairment requiring intubation and mechanical ventilation. UTP is administered in an aerosolized form via an in-line nebulizer, 2–3 times per day, for a total of 5 days. The concentration of UTP is in the range of $10^{-7}$ to $10^{-1}$ moles/liter. Treatment with UTP begins within 12 hours of intubation/mechanical ventilation. The length of treatment for each patient is 5 days.

The safety of UTP to prevent or treat VAP is assessed by standard safety measures of vital signs—heart rate, respiratory rate, blood pressure, electrocardiogram and laboratory blood tests (e.g., blood chemistries, complete blood count, hematology), as well as any adverse events observed.

The effectiveness of UTP in preventing VAP is measured by an absence of symptoms of VAP as determined by periodic physical examinations. Another means of measuring effectiveness is a decrease in the total number of days on mechanical ventilation—this is because an improvement in mucociliary clearance would decrease airway ventilating pressures and the need for assisted ventilation.

The subject methods and compounds described herein provide a means for preventing or treating ventilator-associated pneumonia in the intensive care unit setting. The method comprises administering to the airways of the subject a uridine triphosphate such as uridine 5'-triphosphate (UTP) or any analog of UTP in an amount effective to hydrate mucous secretions or stimulate ciliary beat frequency in the lungs.

The invention now being fully described, it will be apparent to one of ordinary skill in the art that many changes and modifications can be made thereto without departing from the spirit or scope of the appended claims.

What is claimed is:

1. A method of preventing or treating pneumonia, including ventilator-associated pneumonia, in a bedridden or immobilized subject in need of such treatment, said method comprising:

administering to the subject a compound of Formula I, II, III or IV, or a pharmaceutically acceptable salt thereof, in a pharmaceutical carrier having an amount of said compound effective to promote fluid drainage from the airways:

Formula I

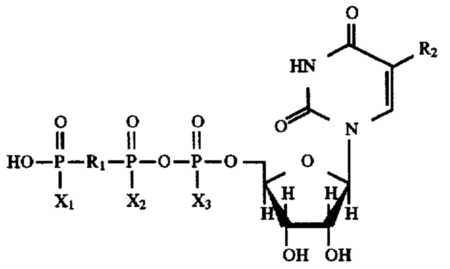

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

Formula II

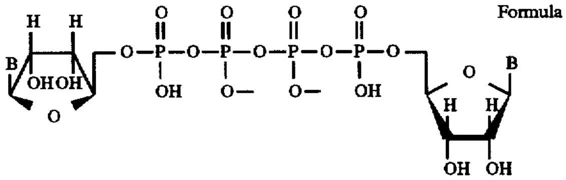

wherein:

$R_1$, $X_1$, $X_2$, and $X_3$ are defined as in Formula I, $R_5$ and $R_6$ are H while $R_7$ is nothing and there is a double bond between N-3 and C-4 (cytosine), or, $R_5$, $R_6$ and $R_7$ taken together are —CH=CH—, forming a ring from N-3 to N-4 with a double bond between N-4 and C-4 ($3,N^4$-ethenocytosine).

2. A method according to claim 1, wherein said compound is delivered by administering a liquid/liquid suspension, including eye drops of said compound to the eyes, or nasal drops, or spray, of said compound to the nasopharngeal airways, nasotracheal tube, endotracheal tube, or tracheostomy of said subject, such that a therapeutically effective amount of said compound contacts the airways of said subject either directly or via systemic absorption and circulation.

3. A method according to claim 1, wherein said compound is delivered by administering an oral form of said compound, such that a therapeutically effective amount of said compound contacts the airways of said subject via systemic absorption and circulation.

4. A method according to claim 1, wherein said compound is delivered by administering a nebulized aerosol or suspension of said compound to the nasopharyngeal airways, nasotracheal tube, endotracheal tube, or tracheostomy of said subject, such that a therapeutically effective amount of said compound contacts the airways of said subject either directly or via systemic absorption and circulation.

5. A method according to claim 1, wherein said compound is delivered by administering a topical form of said compound to the airways via the nose, eyes, outer ear or nasopharyngeal airways of said subject, such
wherein:

B is uracil or adenine, attached as in Formulae I and III;

Formula III

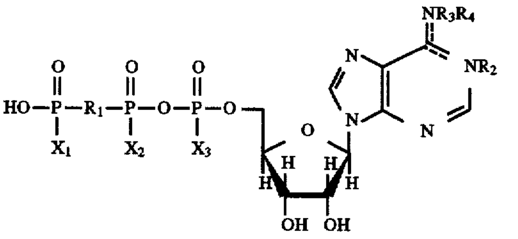

wherein:

$R_1$, $X_1$, $X_2$, and $X_3$ are defined as in Formula I, $R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,$N^6$-ethenoadenine);

Formula IV

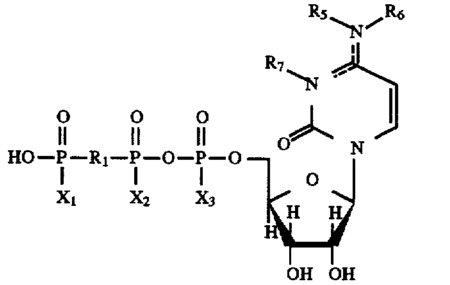

that a therapeutically effective amount of said compound contacts the airways of said subject.

6. A method according to claim 1, wherein said compound is delivered by administering an injected form of said compound, such that a therapeutically effective amount of said compound contacts the airways of said subject either directly or via systemic absorption and circulation.

7. A method according to claim 1, wherein said compound is delivered by administering a suppository form of said compound, such that a therapeutically effective amount of said compound contacts the airways of said subject via systemic absorption and circulation.

8. A method according to claim 1, wherein said compound is delivered by administering an intra-operative instillation of a gel, cream, powder, foam, crystals or liquid suspension form of the active compound such that a therapeutically effective amount of said compound contacts the airways either directly or via systemic absorption and circulation.

9. A method according to claim 1, wherein said compound is delivered by administering a dry-powder aerosolized form of said compound, such that a therapeutically effective amount of said compound contacts the airways of said subject either directly or via systemic absorption and circulation.

10. A method according to claim 1, wherein said compound is administered in an amount sufficient to achieve concentrations thereof on the surfaces of the airways of said subject of from about $10^{-7}$ to about $10^{-1}$ Moles/liter.

11. A method according to claim 1, wherein $X_2$ and $X_3$ are OH.

12. A method according to claim 1, wherein $R_1$ is oxygen.

13. A method according to claim 1, wherein $R_2$ is H.

14. A method according to claim 1, wherein said compound of Formula I is selected from the group consisting of uridine 5'-triphosphate, uridine 5'-O-(3-thiotriphosphate), 5-bromo-uridine 5' triphosphate and the pharmaceutically acceptable salts thereof.

15. A method according to claim 1, wherein said compound of Formula II is selected from the group consisting of $P^1$,$P^4$-di(uridine-5')tetraphosphate ($U_2P_4$) and $P^1$,$P^4$-di (adenosine-5')tetraphosphate ($A_2P_4$) and their 5-substituted derivatives and the pharmaceutically acceptable salts thereof.

16. A method according to claim 1, wherein said compound of Formula III is selected from the group consisting of adenosine 5'-triphosphate, 1,$N^6$-ethenoadenosine 5'-triphosphate, adenosine 1-oxide 5'-triphosphate and the pharmaceutically acceptable salts thereof.

17. A method according to claim 1, wherein said compound of Formula IV is selected from the group consisting of cytidine 5'-triphosphate (CTP), 3,$N^4$-ethenocytidine 5'-triphosphate and the pharmaceutically acceptable salts thereof.

18. A method of preventing or treating sinusitis in a nasally-intubated patient, said method comprising:

administering to the subject a compound of Formula I, II, III or IV, or a pharmaceutically acceptable salt thereof, in a pharmaceutical carrier having an amount of said compound effective to promote mucociliary clearance from the sinuses.

19. A method of preventing or treating retained mucous secretions in a bedridden or immobilized patient, said method comprising:

administering to the subject a compound of Formula I, II, III or IV, or a pharmaceutically acceptable salt thereof, in a pharmaceutical carrier having an amount of said compound effective to promote mucociliary clearance from the airways, and:

placing the subject in a lateral rotation therapeutic bed which mechanically rotates the patient in order to further loosen mucous secretions.

* * * * *

UNITED STATES PATENT AND TRADEMARK OFFICE

CERTIFICATE OF CORRECTION

PATENT NO. : 5,763,447

DATED : June 9, 1998

INVENTOR(S) : Karla M. Jacobus, et al

It is certified that error appears in the above-indentified patent and that said Letters Patent is hereby corrected as shown below:

Columns 11 – 16, should be replaced with the following;

Signed and Sealed this

Tenth Day of April, 2001

Attest:

Nicholas P. Godici

NICHOLAS P. GODICI

Attesting Officer

*Acting Director of the United States Patent and Trademark Office*

UNITED STATES PATENT AND TRADEMARK OFFICE

CERTIFICATE OF CORRECTION

PATENT NO. : 5,763,447
DATED : June 9, 1998
INVENTOR(S) : Karla M. Jacobus, et al It is certified that error appears in the above-identified patent and that said Letters Patent is hereby corrected as shown below:

Columns 11 - 16, should be replace with the following.

Note: This certificate supersedes Certificate of correction issued April 10, 2001

Signed and Sealed this

Twenty-fourth Day of July, 2001

Nicholas P. Godici

*Attest:*

*Attesting Officer*

NICHOLAS P. GODICI
*Acting Director of the United States Patent and Trademark Office* lation. The active compound can be aerosolized in a variety of forms, such as, but not limited to, dry powder inhalants, metered dose inhalants, or liquid/liquid suspensions. In dry powder delivery, the UTP may be formulated alone or in combination with a diluent or carrier, such as sugars (i.e., lactose, sucrose, trehalose, mannitol) or other acceptable excipients for lung or airway delivery. The dry powder may be obtained by methods known in the art, such as spray-drying, milling, freeze-drying, etc.

Another means of administering the active compound to the airways would include any topical form of the active compound, administered as a cream or gel to the nose, eyes or outer ear which would subsequently permeate into the sinus passages of the patient, or administered via a dermal patch, such that a therapeutically effective amount reaches the airways via systemic absorption and circulation.

Another means of administering the active compound to the airways would involve an injected form of the active compound, injected from the chest area or chest tube directly into the lungs.

Another means of administering the active compound to the airways would involve a suppository form of the active compound, such that a therapeutically effective amount of the compound reaches the airways via systemic absorption and circulation.

Another means of administering the active compound would involve intra-operative instillation of a gel, cream, powder, foam, crystal or liquid suspension form of the active compound such that a therapeutically effective amount reaches the airways.

The preferred embodiments of the present invention—UTP and $U_2P_4$, as well as the other compounds for Formulae I–IV also have therapeutic benefit when used in combination with other agents used to treat VAP and retained mucous secretions in immobilized or bedridden patients, such as, but not limited to: antibiotics; antiviral agents; vasoactive agents (such as dopamine, epinephrine, or sodium nitro-prusside); anti-ulcer agents; antacids; analgesics; sedatives; paralytics; anti-platelet adhesion agents (e.g., aspirin, etc.); anti-clotting, blood-thinning agents (e.g., heparin, warfarin, etc.); antihistamine/beta agonist decongestant agents; humidification systems to loosen airway mucus; chest physical therapy and physical activity to do the same; and therapeutic beds which mechanically rotate the patient in order to loosen mucous secretions.

The present invention is further explained in the Example which follows. This example is intended as illustrative of the invention, and is not to be taken as limiting thereof.

EXPERIMENTAL

EXAMPLE 1

Treatment of Patients At Risk For Ventilator-Associated Pneumonia (VAP)

Uridine 5'-triphosphate (UTP) or $P^1,P^4$ di(uridine-5') tetraphosphate ($U_2P_4$) is administered to adult patients with acute neurological impairment requiring intubation and mechanical ventilation. UTP is administered in an aerosolized form via an in-line nebulizer, 2–3 times per day, for a total of 5 days. The concentration of UTP is in the range of $10^{-7}$ to $10^{-1}$ moles/liter. Treatment with UTP begins within 12 hours of intubation/mechanical ventilation. The length of treatment for each patient is 5 days.

The safety of UTP to prevent or treat VAP is assessed by standard safety measures of vital signs—heart rate, respiratory rate, blood pressure, electrocardiogram and laboratory blood tests (e.g., blood chemistries, complete blood count, hematology), as well as any adverse events observed.

The effectiveness of UTP in preventing VAP is measured by an absence of symptoms of VAP as determined by periodic physical examinations. Another means of measuring effectiveness is a decrease in the total number of days on mechanical ventilation—this is because an improvement in mucociliary clearance would decrease airway ventilating pressures and the need for assisted ventilation.

The subject methods and compounds described herein provide a means for preventing or treating ventilator-associated pneumonia in the intensive care unit setting. The method comprises administering to the airways of the subject a uridine triphosphate such as uridine 5'-triphosphate (UTP) or any analog of UTP in an amount effective to hydrate mucous secretions or stimulate ciliary beat frequency in the lungs.

The invention now being fully described, it will be apparent to one of ordinary skill in the art that many changes and modifications can be made thereto without departing from the spirit or scope of the appended claims.

What is claimed is:

1. A method of preventing or treating pneumonia, including ventilator-associated pneumonia, in a bedridden or immobilized subject in need of such treatment, said method comprising:

administering to the subject a compound of Formula I, II, III or IV, or a pharmaceutically acceptable salt thereof, in a pharmaceutical carrier having an amount of said compound effective to promote fluid drainage from the airways:

Formula I

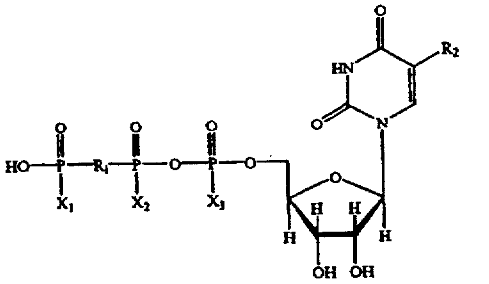

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

Formula II

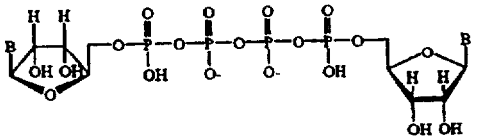

wherein:

B is uracil or adenine, attached as in Formulae I and III;

Formula III

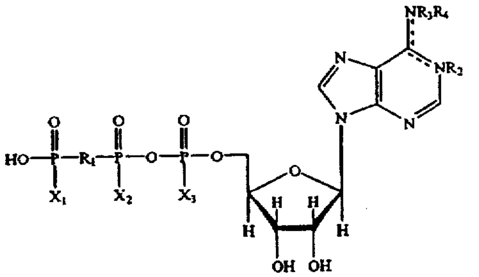

wherein:

$R_1$, $X_1$, $X_2$, and $X_3$ are defined as in Formula I, $R_3$ and $R_4$ are H while $R_2$ is nothing and there is a double bond between N-1 and C-6 (adenine), or $R_3$ and $R_4$ are H while $R_2$ is O and there is a double bond between N-1 and C-6 (adenine 1-oxide), or $R_3$, $R_4$, and $R_2$ taken together are —CH=CH—, forming a ring from N-6 to N-1 with a double bond between N-6 and C-6 (1,$N^6$-ethenoadenine);

Formula IV

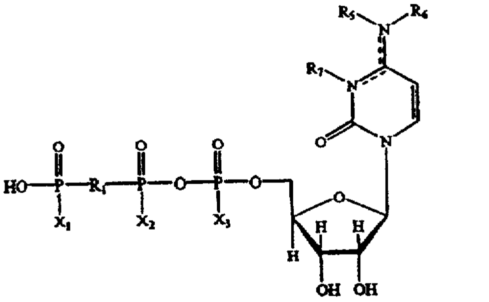

wherein:

$R_1$, $X_1$, $X_2$, and $X_3$ are defined as in Formula I, $R_5$ and $R_6$ are H while $R_7$ is nothing and there is a double bond between N-3 and C-4 (cytosine), or, $R_5$, $R_6$ and $R_7$ taken together are —CH=CH—, forming a ring from N-3 to N-4 with a double bond between N-4 and C-4 (3,$N^4$-ethenocytosine).

2. A method according to claim 1, wherein said compound is delivered by administering a liquid/liquid suspension, including eye drops of said compound to the eyes, or nasal drops, or spray, of said compound to the nasopharngeal airways, nasotracheal tube, endotracheal tube, or tracheostomy of said subject, such that a therapeutically effective amount of said compound contacts the airways of said subject either directly or via systemic absorption and circulation.

3. A method according to claim 1, wherein said compound is delivered by administering an oral form of said compound, such that a therapeutically effective amount of said compound contacts the airways of said subject via systemic absorption and circulation.

4. A method according to claim 1, wherein said compound is delivered by administering a nebulized aerosol or suspension of said compound to the nasopharyngeal airways, nasotracheal tube, endotracheal tube, or tracheostomy of said subject, such that a therapeutically effective amount of said compound contacts the airways of said subject either directly or via systemic absorption and circulation.

5. A method according to claim 1, wherein said compound is delivered by administering a topical form of said compound to the airways via the nose, eyes, outer ear or nasopharyngeal airways of said subject, such that a therapeutically effective amount of said compound contacts the airways of said subject.

6. A method according to claim 1, wherein said compound is delivered by administering an injected form of said compound, such that a therapeutically effective amount of said compound contacts the airways of said subject either directly or via systemic absorption and circulation.

7. A method according to claim 1, wherein said compound is delivered by administering a suppository form of said compound, such that a therapeutically effective amount of said compound contacts the airways of said subject via systemic absorption and circulation.

8. A method according to claim 1, wherein said compound is delivered by administering an intra-operative instillation of a gel, cream, powder, foam, crystals or liquid suspension form of the active compound such that a therapeutically effective amount of said compound contacts the airways either directly or via systemic absorption and circulation.

9. A method according to claim 1, wherein said compound is delivered by administering a dry-powder aerosolized form of said compound, such that a therapeutically effective amount of said compound contacts the airways of said subject either directly or via systemic absorption and circulation.

10. A method according to claim 1, wherein said compound is administered in an amount sufficient to achieve concentrations thereof on the surfaces of the airways of said subject of from about $10^{-7}$ to about $10^{-1}$ Moles/liter.

11. A method according to claim 1, wherein $X_2$ and $X_3$ are OH.

12. A method according to claim 1, wherein $R_1$ is oxygen.

13. A method according to claim 1, wherein $R_2$ is H.

14. A method according to claim 1, wherein said compound of Formula I is selected from the group consisting of uridine 5'-triphosphate, uridine 5'-O-(3-thiotriphosphate), 5-bromo-uridine 5' triphosphate and the pharmaceutically acceptable salts thereof.

15. A method according to claim 1, wherein said compound of Formula II is selected from the group consisting of $P^1$,$P^4$-di(uridine-5')tetraphosphate ($U_2P_4$) and $P^1$,$P^4$-di (adenosine-5')tetraphosphate ($A_2P_4$) and their 5-substituted derivatives and the pharmaceutically acceptable salts thereof.

16. A method according to claim 1, wherein said compound of Formula III is selected from the group consisting of adenosine 5'-triphosphate, 1,$N^6$-ethenoadenosine 5'-triphosphate, adenosine 1-oxide 5'-triphosphate and the pharmaceutically acceptable salts thereof.

17. A method according to claim 1, wherein said compound of Formula IV is selected from the group consisting of cytidine 5'-triphosphate (CTP), 3,$N^4$-ethenocytidine 5'-triphosphate and the pharmaceutically acceptable salts thereof.

18. A method of preventing or treating sinusitis in a nasally-intubated patient, said method comprising:

administering to the subject a compound of Formula I, II, III or IV, or a pharmaceutically acceptable salt thereof, in a pharmaceutical carrier having an amount of said compound effective to promote mucociliary clearance from the sinuses.

19. A method of preventing or treating retained mucous secretions in a bedridden or immobilized patient, said method comprising:

administering to the subject a compound of Formula I, II, III or IV, or a pharmaceutically acceptable salt thereof, in a pharmaceutical carrier having an amount of said compound effective to promote mucociliary clearance from the airways, and:

placing the subject in a lateral rotation therapeutic bed which mechanically rotates the patient in order to further loosen mucous secretions.

* * * * *

US005763447C1

(12) REEXAMINATION CERTIFICATE (4569th)

United States Patent

(10) Number: US 5,763,447 C1

(45) Certificate Issued: May 7, 2002

Jacobus et al.

(54) METHOD OF PREVENTING OR TREATING PNEUMONIA IN IMMOBILIZED PATIENTS WITH URIDINE TRIPHOSPHATES AND RELATED COMPOUNDS

(75) Inventors: Karla M. Jacobus, Cary, NC (US); H. Jeff Leighton, Brookline, MA (US)

(73) Assignee: Inspire Pharmaceuticals, Durham, NC (US)

Reexamination Request:
No. 90/005,969, Apr. 2, 2001

Reexamination Certificate for:

| | |
|---|---|
| Patent No.: | **5,763,447** |
| Issued: | **Jun. 9, 1998** |
| Appl. No.: | **08/685,216** |
| Filed: | **Jul. 23, 1996** |

Certificate of Correction issued Apr. 10, 2001.

Certificate of Correction issued Jul. 24, 2001.

(51) Int. Cl.$^7$ ...................... C07D 473/00; C07D 239/02

(52) U.S. Cl. ...................................................... 514/265

(58) Field of Search ................................ 514/265, 266, 514/269, 274, 382; 544/243, 256, 264, 267, 268, 277, 315

(56) References Cited

U.S. PATENT DOCUMENTS 5,635,160 A 6/1997 Stutts, III et al. ............. 424/45

*Primary Examiner*—Amelia Owens

(57) ABSTRACT

A method of promoting drainage of mucous secretions in the congested airways of a bedridden/immobilized patient or an intubated/mechanically-ventilated patient is disclosed. The method comprises administering to the airways of the patient a uridine phosphate such as uridine 5'-triphosphate (UTP) or $P^1$,$P^4$-di(uridine-5')tetraphosphate, an analog of UTP, or any other analog, in an amount effective to promote drainage of fluid in the congested airways, including sinuses, by hydrating mucous secretions or by stimulating ciliary beat frequency in the airways. Pharmaceutical formulations and methods of making the same are also disclosed. Methods of administering the same would include any liquid suspension (including nasal drops or eye drops or spray), oral form (liquid or pill), aerosol inhalation, powder form, topical, injected, intra-operative instillation or suppository form.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–19 is confirmed.

* * * * *